US007235679B2

(12) United States Patent
Yamauchi (10) Patent No.: US 7,235,679 B2
(45) Date of Patent: Jun. 26, 2007

(54) CRYSTALS OF A VITAMIN D DERIVATIVE AND A METHOD FOR THE PREPARATION THEREOF

(75) Inventor: Tsuyoshi Yamauchi, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/444,360

(22) Filed: Jun. 1, 2006

(65) Prior Publication Data

US 2006/0217354 A1 Sep. 28, 2006

Related U.S. Application Data

(62) Division of application No. 10/821,973, filed on Apr. 12, 2004, now abandoned, which is a division of application No. 10/193,247, filed on Jul. 12, 2002, now Pat. No. 6,831,183, which is a division of application No. 09/202,144, filed as application No. PCT/JP97/02060 on Jun. 16, 1997, now Pat. No. 6,448,421.

(30) Foreign Application Priority Data

Jul. 1, 1996 (JP) ............................. 1996-171321

(51) Int. Cl.
*C07J 9/00* (2006.01)
(52) U.S. Cl. .................................... 552/541
(58) Field of Classification Search ................ 552/541
See application file for complete search history.

(56) References Cited

U.S. PATENT DOCUMENTS

| 3,334,116 A | 8/1967 | Schaaf et al. |
| 4,297,289 A | 10/1981 | DeLuca et al. |
| 4,307,025 A | 12/1981 | DeLuca et al. |
| 4,502,991 A | 3/1985 | DeLuca et al. |
| 4,689,180 A | 8/1987 | DeLuca et al. |
| 4,719,204 A | 1/1988 | DeLuca et al. |
| 5,532,229 A | 7/1996 | Vieth |
| 5,902,806 A | 5/1999 | Ikeda et al. |

FOREIGN PATENT DOCUMENTS

| EP | 0184206 | 6/1988 |
| EP | 0184206 | 11/1988 |
| EP | 0 298757 | 1/1989 |
| EP | 0503630 | 9/1992 |
| EP | 0671411 | 9/1995 |
| JP | 51-15609 A | 2/1976 |
| JP | 08034769 | 2/1996 |
| WO | WO 91/19479 | 12/1991 |
| WO | 9405630 | 3/1994 |
| WO | WO 9412522 | 6/1994 |

OTHER PUBLICATIONS

Miyamoto et al., "Synthetic studies of vitamin D analogues. XIV. Synthesis and calcium regulating activity of vitamin D3 analogues bearing a hydroxyalkoxy group at 2beta-position.", Chem. Pharm. Bull., vol. 41(6), pp. 1111-1113, 1993.*
Wahyuni, W, and K. Jinno, "Separation of Fat-Soluble Vitamins with Polymer-Coated Silica-Based Octadecyl Bonded Phase in Reversed-Phase Liquid Chromatography", Journal of High Resolution Chromatography & Chromatography Communications. (1987). 10(8):464-465.
Miyamoto, et al., "SYnthetic Studies of Vitamin D Analogues. XIV. Synthesis and Calcium Regulating Activity of Vitamin D Analogues Bearing a Hydroxyalkoxy Group at 2B-Position," Chem. Pharm. Bull., 41(6):1111-1113 (1993).
Posner, et al., "Sterecontrolled Total Synthesis of Calcitriol Derivatives: 1,25-Dihydroxy-2-(4-hydroxybuty) vitamin D Analogs of an Osteoporosis Drug," J. Org. Chem. 59:7855-7861 (1994).
Barner, et al., "87. Zur Konfiguration des Vitamin-D-Metaboliten 25,26-Dihydroxycholecaciferol: Synthese von (25S,26)-und (25R-26)-Dihydroxycholecalciferol," Helvetica. Chimica. Acta. 64:915-938 (19981).
XP-002102280, Chemical Abstract, 124:1306, (1996).
XP-002102281, Derwent Publication Ltd., (1995).
Chemical Abstracts 124(7);225 (1996), 124:77311p.
Chemical Abstracts, vol. 124, No. 7, 77313, (1996).

* cited by examiner

*Primary Examiner*—Barbara P. Badio
(74) *Attorney, Agent, or Firm*—Browdy and Neimark, PLLC (57) ABSTRACT

The present invention provides crystals of the compound represented by formula (I):

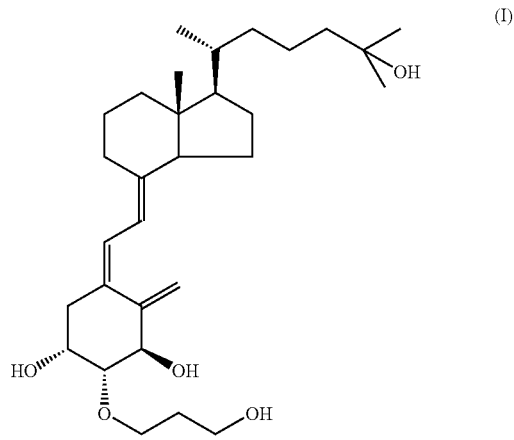

crystals of a vitamin D derivative which are obtained by purifying a crude or preliminarily purified product of the vitamin D derivative through a reverse phase chromatography and then crystallizing the purified derivative from an organic solvent; novel compounds which are formed during the synthesis of a vitamin D derivative as by-product; and a method for purifying a vitamin D derivative or the precursor thereof. The method of the present invention makes it possible to supply a highly purified vitamin D derivative, especially ED-71, in bulk and steadily.

2 Claims, 4 Drawing Sheets

Structure of ED-71 (2); Stereographic view

Figure 3

Structure of ED-71 where hydrogen bonds are focused (1)

Figure 4

Structure of ED-71 where hydrogen bonds are focused (2);
Stereographic view

CRYSTALS OF A VITAMIN D DERIVATIVE AND A METHOD FOR THE PREPARATION THEREOF

CROSS-REFERENCE TO RELATED APPLICATIONS

This is a divisional of parent application Ser. No. 10/821,973, filed Apr. 12, 2004, now abandoned, which is a divisional of Ser. No. 10/193,247, filed Jul. 12, 2002, now U.S. Pat. No. 6,831,183, which is a divisional of Ser. No 09/202,144, filed Dec. 9, 1998, now U.S. Pat. No. 6,448,421, which is the national stage under 35 U.S.C. Section 371 of International Application PCT/JP97/02060 filed Jun. 16, 1997, and claiming priority from Japanese application 171321/1996 filed Jul. 1, 1996.

TECHNICAL FIELD

The present invention relates to novel crystals of a vitamin D derivative and, more specifically, to novel crystals of a vitamin D derivative which are obtained by purifying the vitamin D derivative through a reverse phase chromatography and then crystallizing the purified derivative from an organic solvent. The present invention also relates to a method for purifying a vitamin D derivative which comprises a crystallization step.

BACKGROUND ART

A variety of vitamin D derivatives are known to have useful physiological activities. For example, JP 6-23185B/1994 discloses that a 1α-hydroxyvitamin $D_3$ derivative represented by the following general formula:

wherein $R_1$ denotes an amino group or the formula OR' where R' denotes a lower alkyl group having 1 to 7 carbon atoms which is unsubstituted or substituted by a hydroxyl group, a halogen atom, a cyano group or an acylamino group, and $R_2$ denotes a hydrogen atom or a hydroxyl group, is useful as a therapeutic agent for diseases caused by calcium dysbolism or as an anti-tumor agent.

1α,25-dihydroxy-2β-(3-hydroxypropoxy)vitamin $D_3$ (also called as ED-71) which is one of the compounds covered by the above general formula is an active form of a vitamin D derivative having a bone forming action and thus is in a way to be developed as a therapeutic agent for osteoporosis.

Once such a vitamin D derivative is established as a therapeutic agent, it should be highly purified and be supplied in bulk and steadily. Therefore, it is desired to establish a method for manufacturing a vitamin D derivative as soon as possible.

In particular, ED-71 has been obtained only in an amorphous form and there is no reported isolation of ED-71 in a crystalline form.

DISCLOSURE OF THE INVENTION

An object of the present invention is to establish a method for preparing a highly purified vitamin D derivative, especially ED-71, which makes it possible to supply the product in bulk and steadily.

Another object of this invention is to provide crystals of a vitamin D derivative which may be obtained by purifying a crude or preliminarily purified product of the vitamin D derivative.

Another object of this invention is to provide a method for purifying a vitamin D derivative which comprises a crystallization step.

A further object of this invention is to provide a method for purifying the pre form compound of ED-71, which comprises a crystallization step, and to provide a purified pre form compound obtained by the method.

A still further object of this invention is to provide novel compounds which are secondarily formed during the synthesis and purification of a vitamin D derivative.

We have conducted extensive research on the following points which are issued during the synthesis and purification of ED-71 from its provitamin D derivative (pro form): (1) the effect of impurities in the pro form on the HPLC preparative purification of ED-71; (2) the stability of ED-71 and its previtamin D derivative (pre form) to heat, light and oxygen; (3) the handling of ED-71 which exhibits a high physiological action even in a extremely small dose; and (4) the possibility of the purification of ED-71 by crystallization. As a result of the research, we have found that crystals of ED-71 can be obtained in gram order by recrystallizing the pro form from methanol, subjecting the recrystallized pro form to a photo-reaction at a low temperature and then a thermal isomerization reaction, purifying the isomerized product by a reverse phase HPLC, concentrating the eluate, and then crystallizing the residue from ethyl acetate, and have completed the present invention. Further, we have determined the structure of by-products which are originally contained in the pro form or formed during the photo-reaction and found that some compounds of them are novel.

According to one aspect of the present invention, crystals of the compound represented by formula (I):

are provided.

According to another aspect of the present invention, crystals of a vitamin D derivative which are obtained by purifying a crude or preliminarily purified product of the vitamin D derivative through a reverse phase chromatography and then crystallizing the purified derivative from an organic solvent, are provided.

According to a further aspect of the present invention, a method for purifying a vitamin D derivative which comprises subjecting the vitamin D derivative to a reverse phase chromatography is provided.

According to a further aspect of the present invention, a method for purifying a vitamin D derivative which comprises crystallizing the vitamin D derivative from an organic solvent is provided.

According to a further aspect of the present invention, a method for purifying a vitamin D derivative which comprises purifying a crude or preliminarily purified product of the vitamin D derivative through a reverse phase chromatography and then crystallizing the purified derivative from an organic solvent is provided.

According to a further aspect of the present invention, a method for purifying the compound represented by formula (II):

which comprises recrystallizing a crude or preliminarily purified product of the compound represented by formula (II) from an alcohol is provided.

According to a further aspect of the present invention, a purified product of the compound represented by formula (II):

which is obtained by recrystallizing a crude or preliminarily purified product of the compound represented by formula (II) from an alcohol is provided.

According to a further aspect of the present invention, a method for preparing a purified product of the vitamin D derivative represented by formula (I):

which comprises recrystallizing a crude or preliminarily purified product of the compound represented by formula (II):

from an alcohol, subjecting the recrystallized compound of formula (II) to an ultraviolet light radiation and then a thermal isomerization reaction to give a vitamin D derivative represented by formula (I), purifying the crude or preliminarily purified vitamin D derivative of formula (I) through a reverse phase chromatography, and crystallizing the vitamin D derivative of formula (I) from an organic solvent, is provided.

According to a still further aspect of the present invention, the compound represented by formula (III):

and the compound represented by formula (IV):

are provided. These compounds are contained in the reaction mixture obtained by the ultraviolet light radiation and the subsequent thermal isomerization reaction of the pro form of ED-71.

PREFERRED EMBODIMENTS OF THE INVENTION

As used herein, the term "vitamin D derivative" means a compound having the partial structure of formula (V):

The vitamin D derivative is preferably the compound represented by formula (VIA), (VIB) or (VIC):

wherein $R_1$ denotes (1) an amino group; (2) —$OR_5$ where $R_5$ is a lower alkyl, a lower alkenyl or a lower alkynyl group, each of which may be substituted by a hydroxyl group, a halogen atom, a cyano group, an amino group, an acylamino group or a lower alkoxy group; or (3) a lower alkyl group, a lower alkenyl group or a lower alkynyl group, each of which may be substituted by a hydroxyl group, a halogen atom, a cyano group, an amino group, an acylamino group or a lower alkoxy group; $R_2$, $R_3$ and $R_4$ each denotes an alkyl group having 1 to 10 carbon atoms, an alkenyl group having 2 to 10 carbon atoms, or an alkynyl group having 2 to 10 carbon atoms, each of which may be substituted by one or more hydroxyl groups; and A denotes a sulfur or oxygen atom.

In the above definition of substituents, the term "lower" means the number of carbon atoms contained in the group qualified by the term, for example, 1 to 7 for alkyl group, 2 to 7 for each of alkenyl and alkynyl groups, and 1 to 7 for alkoxy group.

The vitamin D derivative is more preferably 1α-hydroxyvitamin $D_3$, 1α,25-dihydroxyvitamin $D_3$, 24,25-dihydroxyvitamin $D_3$, or the compound represented by formula (VIIA) or (VIIB):

(VIIA)

(VIIB)

wherein n denotes an integer of 1 to 7, or the compound represented by formula (VIIIA) or (VIIIB):

(VIIIA)

(VIIIB)

wherein A denotes a sulfur or oxygen atom.

Especially preferred vitamin D derivative is the compound represented by formula (VIIA):

(VIIA)

wherein n denotes an integer of 1 to 7.

The most preferred vitamin D derivative is the compound represented by formula (IX):

(IX)

which is also called as ED-71.

As used herein, the term "crystal" is used in its broadest meanings and thus is not limited by the crystal form, the crystal system or the like.

Crystals of ED-71 which is the most preferred vitamin D derivative of the present invention is not limited by any physical property, as stated previously. However, they are particularly preferred to have the following properties: (1) Appearance: white crystalline powder on a visual or fluorescent-microscopic inspection; (2) Solubility: completely soluble at a concentration of 1 mg/mL in ethanol; (3) Identification means: IR or NMR method; (4) Melting point: 130 or higher as measured by DSC; (5) Absorbance index: $\epsilon=16000$ or higher as measured at a concentration of 40 μg/mL in ethanol at 265 nm; and (6) HPLC purity: 97% or higher on the basis of the area under the peak of ED-71 relative to that under the total peaks recorded in HPLC under the following conditions; DIACHROMA ODS N-20 5 μm 4.6×250 mm, 45% acetonitrile-water, a flow rate of 1 mL/min, 220 nm, 1 mg/mL 10 μL, 4-90 minutes.

According to one aspect of the present invention, crystals of a vitamin D derivative which may be obtained by purifying a crude or preliminarily purified product of the vitamin D derivative through a reverse phase chromatography and then crystallizing the purified derivative from an organic solvent, as well as a method for purifying a vitamin D derivative which comprises subjecting the vitamin D derivative to a reverse phase chromatography and/or crystallizing the purified vitamin D derivative from an organic solvent are provided.

As used herein, the term "crude or preliminarily purified product" means a vitamin D derivative product which is obtained from the synthesis of the vitamin D derivative without or with a conventional purification immediately after the synthesis reaction, and it is usually in an amorphous form.

As used herein, the term "reverse phase chromatography" means the chromatography system in which the stationary phase has a polarity lower than the mobile phase. A high performance liquid chromatography (HPLC) is preferred as the reverse phase chromatography.

It will be necessary to appropriately choose eluent, column packing and load onto the column in order to effectively separate the substance of interest.

Examples of the eluent include, but not limited to, acetonitrile/water and acetonitrile/methanol/water. The mixing ratio of the solvents used for the above mentioned eluents will vary depending upon such factors as the substance to be purified and column packing to be used and thus an optimum ratio of the solvents for a specific application may be determined by one of ordinary skill in the art. The ratio of acetonitrile/methanol/water will generally fall within the range of 20-60/0-40/0-80 parts by weight.

The column packing may be chosen in respect to its particle diameter and pore size while taking the compatibility of the column packing with the substance to be purified and the column to be used into consideration.

The load onto the column will also vary depending on the internal diameter of the column and the like. However, the load may be, for example, about 25 μg to 10 g, preferably about 25 μg to 3 g when the internal diameter is 50 mm.

The fraction obtained by carrying out the chromatography as described above should be treated to isolate the solute contained in the fraction prior to crystallization. The procedures for isolation includes evaporation, freeze-drying, extraction and filtration. From these procedures for isolation, one can choose one or more procedures suitable to the substance to be purified by considering the properties of the substance. For example, an evaporation is operationally advantageous for the purification of ED-71, since it is reproducible and ED-71 is not decomposed.

The organic solvent which may be used for the crystallization of the vitamin D derivative is preferably an aprotic organic solvent. Examples of the aprotic organic solvent include esters such as ethyl acetate, ketones such as acetone, ethers such as diethyl ether and diisopropyl ether, acetonitrile, and a mixture thereof, preferably ethyl acetate, acetone, acetonitrile, and a mixture thereof.

Crystallization conditions will vary depending on such factors as the substance to be purified and the solvent to be used and thus suitable conditions for a specific application may be determined by one of ordinary skill in the art. However, the crystallization will be generally carried out by using a solvent in an amount 1-100 times and preferably 5-10 times more than a crude vitamin D derivative at a temperature of not higher than 30° C. and preferably not higher than −10° C.

According to one aspect of the present invention, a method for purifying the compound represented by formula (II):

which comprises recrystallizing a crude or preliminarily purified product of the compound from an alcohol, as well as the compound of formula (II) purified by the method are provided.

The alcohol used for this recrystallization is methanol.

The physical properties of the compound represented by formula (II) which has been purified by the recrystallization from an alcohol as above is not limited to any values. However, it is particularly preferred to have the following properties: (1) Appearance: from white to yellow crystalline powder on a visual or fluorescent-microscopic inspection; (2) Solubility: completely soluble at a concentration of 2 mg/mL in ethanol (the solution may be from water-white to yellow); (3) Identification means: IR and NMR methods; (4) Water content: 3.0% or lower as measured by Karl-Fischer method using 100 mg of sample; (5) Absorbance index: $\epsilon=10000$ or higher as measured at a concentration of 100 μg/mL in ethanol at 282 nm; (6) HPLC purity: 85% or higher on the basis of the area under the peak of the compound represented by formula (II) relative to that under the total peaks recorded in HPLC and no observable peak between the peaks of the pro form and $unP_4$ in the HPLC under the following conditions; DIACHROMA ODS N-20 5 μm 4.6× 250 mm, 55% acetonitrile-water, a flow rate of 1 mL/min, 220 nm, 1 mg/mL 10 μL, 4-70 minutes; and (7) Content: 85% or higher in HPLC carried out using an internal standard under the following conditions; YMC Pack ODS A-303 5 μm 4.6×250 mm, 55% acetonitrile-water, a flow rate of 1 mL/min, 220 nm.

The following examples are provided in order to further illustrate the present invention but should not be construed as limiting the scope thereof.

EXAMPLES

Example 1

Synthesis and Purification of 2β-(3'-hydroxypropoxy)-5,7-cholestadiene-1α,3β-triol (pro form)

epoxy compound (1)

pro form (2)

A mixture of epoxy compound (1) (1.00 g, 2.41 mmol), potassium tert-butoxide (0.75 g, 6.68 mmol) and 1,3-propanediol (20 ml) was stirred at room temperature for 10 minutes. Then, the reaction mixture was heated to an internal temperature of 95° C. and stirred for 5 hours at this temperature. The reaction mixture was poured into a saturated aqueous solution of ammonia (40 ml) with stirring. After stirring at room temperature (25-35° C.) for 10 minutes, crystals formed were collected on a filter and washed with distilled water (20 ml) three times. The crude crystals containing water (6.3 g) were stirred in acetonitrile (20 ml) at room temperature (27-22° C.) for 1 hour. The crystals were collected on a filter and washed with acetonitrile (5 ml) twice and then dried to give the pro form compound (2) (0.96 g, 81% yield).

The pro form compound (2) thus obtained (29.0 g) was heated to dissolve in methanol (290 ml) previously pretreated by passing argon gas and then the resulting solution was filtered through a Kiriyama filter paper (No. 4) while hot. After cooling to room temperature, a seed was added to the solution to induce crystallization. After further cooling to below −10° C., crystals thus formed were collected on a filter and washed with 29 ml of cold methanol twice. Then, the crystals were dried in vacuo at room temperature to give 22.9 g of purified pro form (79.1% recovery, 92.1% net recovery). The physical data of the purified pro form are as follows:

NMR (CD$_3$OD) and IR (KBr): indicated to be the title compound;
TLC (CH$_2$Cl$_2$:EtOH=9:1): only one spot developed (Rf 0.5);
HPLC purity (220 nm): 98.7%;
Content: 97.1% (internal standard method); and
DSC: peak min. 95.6° C. and 163.2° C., peak max. 120.2° C.

Example 2

Synthesis and Purification of (1R,2R)-1,25-dihydroxy-2-(3'-hydroxypropoxy)-cholecalciferol; 2β-(3'-hydroxypropoxy)-(1α,3β,5Z,7E)-9,10-secocholesta-5,7,10(19)-triene-1,3,25-triol (ED-71)

pro form (2)

pre form

ED-71

The purified pro form (2) obtained in Example 1 (6.02 g) was dissolved in THF (1L) in a 1L vessel and the solution was UV light-irradiated with 400 W lamp having a high pressure of mercury vapor through a Vycor filter at a cooled condition (an internal temperature of below −13° C.) for 150 minutes under a stream of argon. After allowing to rise to room temperature, the reaction solution was poured from the vessel into a 2L eggplant type flask while the vessel was washed with fresh THF (100 mL). The combined solution was heated under reflux for 180 minutes. After concentrating the reaction mixture, the resulting residue was dissolved in methanol (80 mL) to form a separation sample. Using a pump, 20 mL of the sample containing 1.5 g of solute as calculated and expressed as the pro form was placed on the preparative chromatography column having a internal diameter of 50 mm and a length of 300 mm and packed with DIACHROMA ODS N-20 having a particle diameter of 5 µm which is commercially available from Mitsubishi Kakouki Co.). 45% acetonitrile in water was passed through the column at a flow rate of 60 ml/min and the eluate was monitored with UV-light at 220 and 305 nm. About 2.4 L ED-71-containing fractions were collected for the time period from about 130 to 170 minutes after starting the chromatography. This series of procedures was repeated a further 3 times, the pooled fractions of ED-71 being about 9 L in total. The combined fractions were then concentrated using 10 L rotary evaporator. The residue was dissolved in ethanol and the solution was evaporated to dryness again. The resulting residue was then taken up with ethyl acetate (20 ml) and the solution was stirred at room temperature to precipitate crystals. The suspension was further cooled to below −10° C. and stirred for 15 minutes at this temperature. The crystalline material was filtered off, washed with cooled ethyl acetate (6 ml) three times, and dried in vacuo at room temperature overnight to give ED-71 (2.17 g, 36.1% yield).

HPLC purity: 99.8% (220 nm), 99.9% (265 nm)

UV (EtOH): $\lambda_{max}$ 265.4 nm ($\epsilon$17100)

DSC: 135.3° C. (peak min), 122 mJ/mg

Residual solvent (GC method): 1.24% (EtOAc), 0.24% (EtOH)

IR (cm$^{-1}$): 3533, 3417, 3336, 2943, 2918, 2862, 1649, 1470, 1444, 1416, 1381, 1377, 1342, 1232, 1113, 1078, 1072, 1045, 999, 974, 957, 955, 924, 910, 895, 868, 833, 796, 764, 663, 634, 594, 472

Example 3

Physical Data of Related Compounds

Some analogues which were formed during the photo- and thermal isomerization reactions were isolated and structurally determined and then characterized. ED-71 and the pro form thereof obtained in Examples 1 and 2 were also characterized in detail. Note that the physical data reported below are from samples further purified by recrystallization and the like of the analogues.

Melting points are not corrected. IR spectra were determined in JEOL JIR-6000 by KBr tablet method. $^{1}$H-NMR and $^{13}$C-NMR spectra were determined through utilization of JEOL JNM-270EX. TMS was used as an internal standard for $^{1}$H-NMR and a peak of CHCl$_3$ was used as a standard for $^{13}$C-NMR. UV were determined through utilization of HITACHI U-3210 in ethanol at room temperature.

Physical data of pro form of ED-71 which was obtained in Example 1:

$^{1}$H-NMR (ppm): 0.63(3H,s), 0.96(3H, d, $J^{20-21}$=6.3 Hz), 1.07(3H, s), 1.22 (6H, s), 3.6-4.0(7H, m), 5.36-5.40 (1H, m), 5.70-5.73(1H, m)

$^{13}$C-NMR (ppm): 141.1, 136.6, 120.8, 115.1, 82.2, 71.0, 70.9, 68.3, 66.7, 59.8, 55.7, 54.4, 44.1, 42.9, 41.3, 39.0, 38.3, 36.3, 36.0, 34.6, 32.0, 28.8, 28.7, 27.9, 22.9, 20.7, 20.5, 18.6, 15.8, 11.7

UV; $\lambda_{max}$ ($\epsilon$): 294.2 nm (6550), 282.2 nm (11300), 271.9 nm (10500), 204.7 nm (2420)

IR (cm$^{-1}$): 3385, 2941, 2872, 1471, 1468, 1381, 1379, 1327, 1138, 1082, 1080, 1053

Physical data of ED-71:

$^{1}$H-NMR (ppm): 6.37(1H, d; 11.4 Hz), 6.05(1H, d; 11.4 Hz), 5.50(1H, t; 2.1 Hz), 5.08(1H, t; 2.1 Hz), 4.32(1H, d; 8.9 Hz), 4.26(1H, m), 3.88-3.96(1H, m), 3.85(2H, t; 5.7 Hz), 3.69-3.77(1H, m), 3.27(1H, dd; 9.0 Hz, 2.8 Hz), 2.78-2.83(1H, m), 2.55(1H, dd; 10.6 Hz, 4.0 Hz), 2.42(1H, bd; 13.6 Hz), 1.8-2.1(5H, m), 1.22(6H, s), 1.2-1.7(11H, m), 0.94(3H, d; 6.3 Hz), 0.9-1.1(1H, m), 0.55(3H, s)

$^{13}$C-NMR (ppm): 144.2, 143.0, 132.2, 124.9, 117.2, 111.8, 85.4, 71.6, 71.1, 68.3, 66.6, 61.1, 56.6, 56.4, 45.9, 44.4, 40.5, 36.4, 36.1, 31.9, 29.3, 29.2, 29.1, 27.7, 23.7, 22.4, 20.8, 18.8, 11.9

UV; $\lambda_{max}$: 265.4 nm ($\epsilon$17900)

Melting point: 134.8-135.8° C. (1° C./min),

DSC: 137° C. (peak min, 115 mJ/mg),

TG/DTA: 138° C. (peak min, dry weight loss on melting: about 1%, test sample 1.96 mg), IR (cm$^{-1}$): 3533, 3417, 3336, 2943, 2918, 2862, 1649, 1470, 1444, 1416, 1381, 1377, 1342, 1232, 1113, 1078, 1072, 1045, 999, 974, 957, 955, 924, 910, 895, 868, 833, 796, 764, 663, 634, 594, 472

Lumi form of ED-71 which is represented by the formula:

(IV)

HPLC purity: 97.5% (220 nm)

$^{1}$H-NMR (ppm): 5.75(1H, d, J=5.3 Hz), 5.42-5.44(1H, m), 4.19(1H, q, J=2.9 Hz), 3.8-4.0(4H, m), 3.6-3.7(1H, m), 3.25(1H, dd, J=2.6 Hz, 9.6 Hz), 1.21(6H, s), 0.90(3H, d, J=5.6 Hz), 0.82(3H, s), 0.58(3H, s)

$^{13}$C-NMR (ppm): 141.9, 136.2, 123.3, 115.5, 82.8, 77.9, 71.1, 67.4, 64.9, 61.1, 57.2, 49.5, 46.7, 44.4, 43.8, 41.4, 37.5, 36.2, 35.9, 32.0, 29.4, 29.2, 28.8, 22.6, 21.4, 20.9, 18.5, 18.3, 8.5

UV; $\lambda_{max}$: 273.5 nm ($\epsilon$9010)

IR (cm$^{-1}$): 3437, 3383, 3309, 3041, 2960, 2935, 2872, 2787, 1657, 1641, 1470, 1441, 1375, 1257, 1205, 1203, 1167, 1128, 1097, 1074, 1039, 1011, 980, 935, 908, 885, 820, 781, 779, 723, 671, 613

Tachy form of ED-71 which is represented by the formula:

(III)

HPLC purity: 97.6% (220 nm)
$^1$H-NMR (ppm): 6.65 (1H, d, J=16.1 Hz), 6.10 (1H, d, J=16.1 Hz), 5.73(1H, d, J=2.8 Hz), 4.21-4.25(2H, m), 3.70-3.90(4H, m), 3.45(1H, dd, J=2.4 Hz, 6.0 Hz), 1.91(3H, s), 1.22(6H, s), 0.98(3H, d, J=6.5 Hz), 0.69 (3H, s)
$^{13}$C-NMR (ppm): 138.1, 130.9, 129.5, 127.8, 126.0, 124.5, 83.1, 72.4, 71.1, 68.5, 65.3, 61.1, 54.0, 50.0, 44.4, 42.8, 36.4, 36.0, 35.9, 31.9, 31.4, 29.4, 29.2, 28.7, 25.1, 24.3, 20.8, 18.7, 15.1, 11.2
UV; $\lambda_{max}$: 281.4 nm ($\epsilon$26100)
IR (cm$^{-1}$): 3375, 2945, 2875, 1664, 1632, 1612, 1468, 1429, 1377, 1215, 1157, 1095, 1068, 957, 908, 879, 764, 710, 646

Pre form of ED-71 which is represented by the formula:

HPLC purity:97.2% (220 nm)
$^1$H-NMR (ppm):5.91, 5.78(1H×2, d, J=12 Hz), 5.52(1H, d, J=3.3 Hz), 4.0-4.2(2H, m), 3.7-4.0(4H, m), 3.43(1H, dd), 1.76(3H, s), 1.22(6H, s), 0.96(3H, d, J=6.6 Hz), 0.70(3H, s)
UV; $\lambda_{max}$:206 nm ($\epsilon$10300)
IR (cm$^{-1}$):3377, 2949, 2947, 2872, 1643, 1470, 1435, 1406, 1379, 1377, 1263, 1215, 1140, 1119, 1088, 1063, 1047, 1032, 1030, 962, 937, 935, 756, 735, 542

Example 4

X-ray Crystal Structure Analysis of ED-71

X-ray diffraction experiments of ED-71 were conducted using a crystalline powder selected from the sample powders, a part of which was also used in Example 3. As a result, the crystal was found to be of rhombic system and have a space group of $P2_12_12_1$ and lattice constants of a=10.352 (2), b=34.058 (2) and c=8.231 (1)Å, and Z=4. From these experiments, 2520 reflection data were obtained.

A structure analysis was made as follows. A direct method using SHELXS86 was employed in determining phases and then the location of each of the non-hydrogen atoms was determined by a Fourier mapping. For the carbon-bonded hydrogen atoms, each location of them was determined by a calculation using the location of the carbon atom. For the oxygen-bonded hydrogen atoms, each location of them was determined by a D mapping after each location of other atoms was determined.

After improving the preciseness of the locations of the non-hydrogen and oxygen-bonded hydrogen atoms and the temperature factor of anisotropy for the non-hydrogen atoms by the method of least squares, the reliability factor (R value) of the analysis results converged into 3.9%. However, the absolute structure of the crystal was not determined from the results directly but by further calculating the results on condition that the configuration of positions 13, 14, 17 and 20 of ED-71 is the same as the corresponding configuration of cholesterol.

Figure 1:
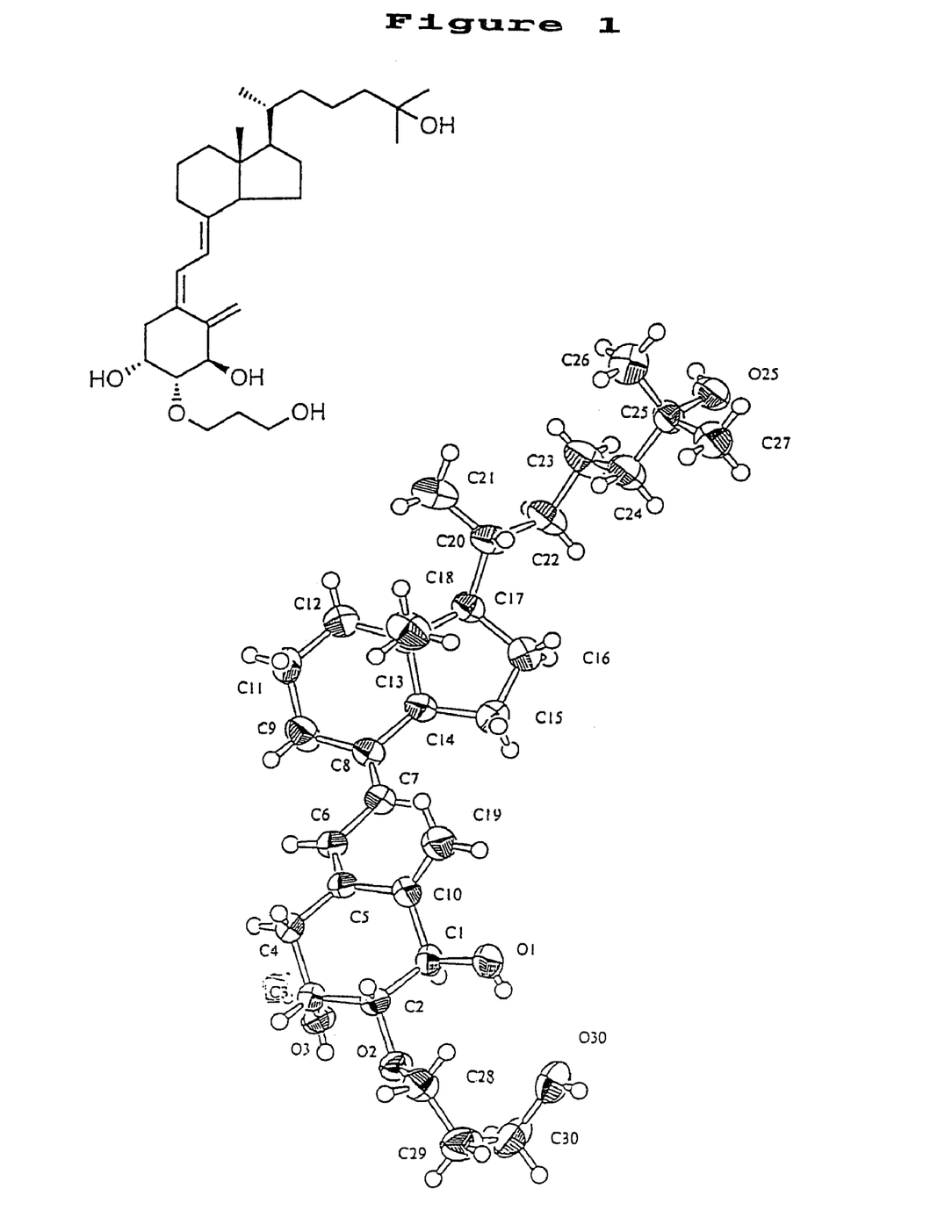
FIG. 1 is a molecular structure projective view showing the structure of ED-71 crystal.
Figure 2:
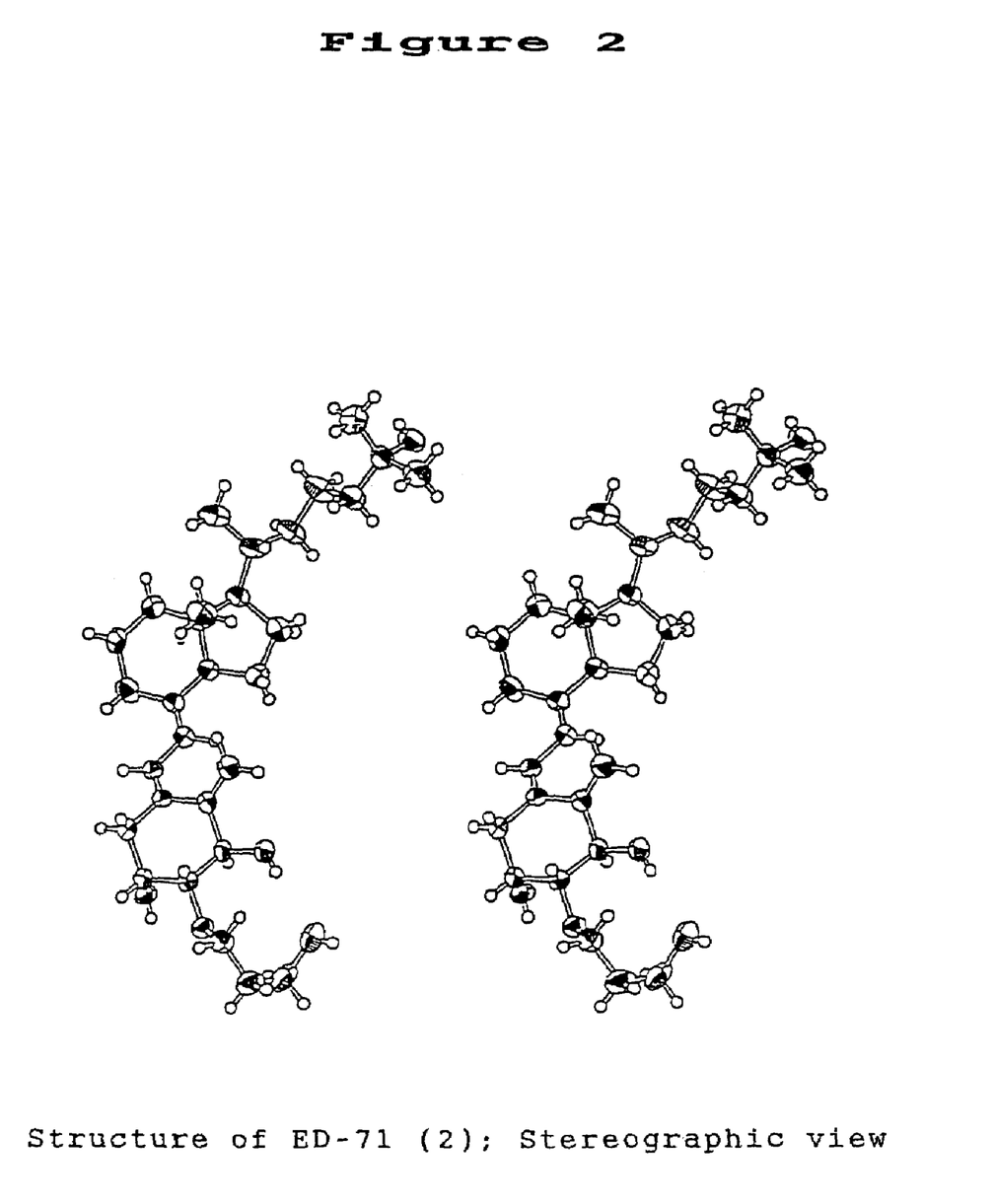
FIG. 2 is a molecular structure stereographic projective view showing the structure of ED-71 crystal.
Figure 3:
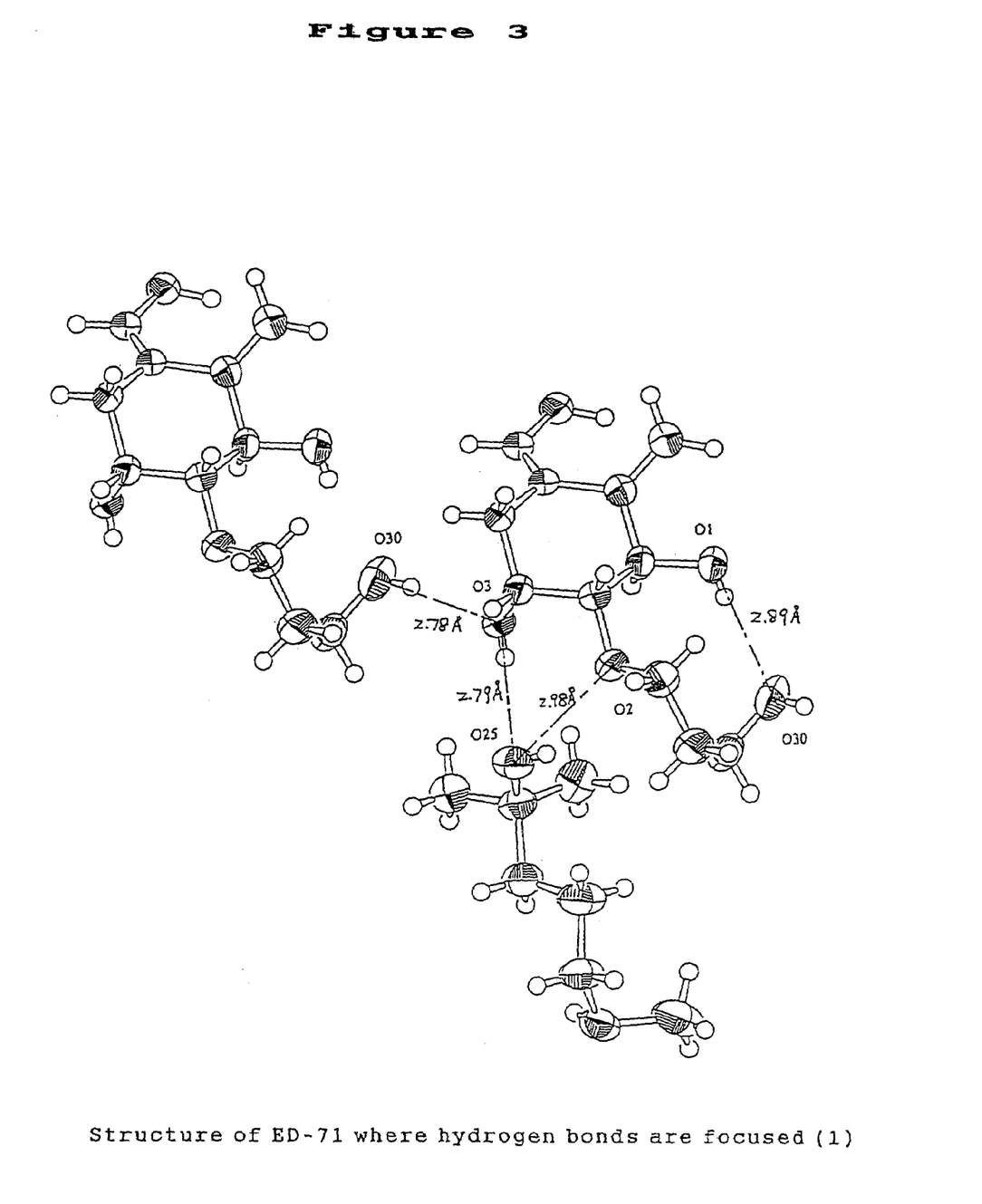
FIG. 3 is a molecular structure projective view showing the structure of ED-71 crystal where hydrogen bonds are focused.
Figure 4:
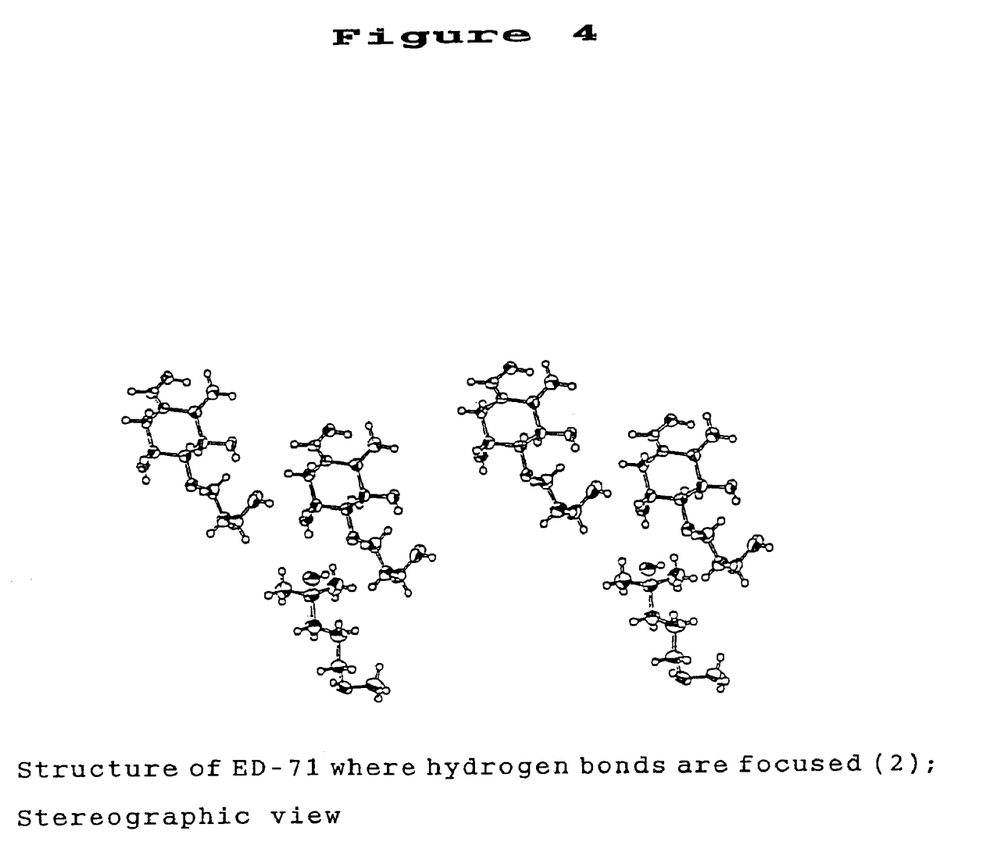
FIG. 4 is a molecular structure projective view showing the structure of ED-71 crystal where hydrogen bonds are focused.

FIGS. 1 to 4 show the structure of ED-71 and the hydrogen bonds therein, respectively, which were determined on the basis of the analysis results.

Reference Example 1

Stability of ED-71 Crystalline Compound

Amorphous and crystalline ED-71 compounds were tested for stability at 10, 25 and 40. To estimate the stability, HPLC quantitative assay and absorbance and purity measurements were utilized. The purity was expressed as peak area ratio in percentage in HPLC (% P.A.R.). The test was carried out by using the following procedures:

(1) Procedures of the Stability Test

About 2 mg portions of each of the amorphous and crystalline samples are precisely weighed into transparent 10 ml test tubes each having screw cap, individually.

The test tubes are purged with argon using a vacuum desiccator and a glove box. This purging procedure is not applied to the test tubes indicated as "1 M (air)" in the tables below.

The test tubes in groups are fixed in thermostatic baths which are respectively controlled at the above temperatures and allowed to stand in the dark. After one (1 W) or two (2 W) weeks or one month (1 M), the test tubes are removed from the baths and subjected to the following assay and measurements:

(2) HPLC Quantitative Assay 5 ml of absolute ethanol is precisely added to the test tube to form a sample solution. 1 ml of the sample solution and 1 ml of an internal standard solution are both precisely added to another test tube and the resulting mixture is diluted with methylene chloride to give a whole volume of 20 ml. This diluted solution is designated solution 1. The internal standard solution is formed by dissolving 2-aminopyrimidine in methanol to a concentration of 0.6 mg/ml.

Next, both of 1 ml of another standard solution for quantitative assay which is formed by dissolving crystalline ED-71 in absolute ethanol to a concentration of 0.4 mg/ml and 1 ml of the internal standard solution are precisely added to another test tube and the resulting mixture is diluted with methylene chloride to give a whole volume of 20 ml. This diluted solution is designated solution 2.

HPLC is carried out using 20 μl of each of solutions 1 and 2. For each solution, an area ratio of the peak of ED-71 to the peak of the internal standard substance is determined from the HPLC data. The ED-71 content in the sample is determined from the ratio of the area ratio for solution 1 to that for solution 2.

Survivability (%) is determined by dividing the ED-71 content thus obtained by ED-71 content in the same sample but prior to the above treatment.

HPLC conditions used:
Column: YMC A-004SIL (4.6×300 mm)
Mobile phase: methylene chloride/methanol mixture (95/5)
Flow rate: 1 ml/min
Detection: at UV 265 nm.

(3) Absorbance Measurement 1 ml of the sample solution as prepared in "HPLC quantitative assay" above is diluted with absolute ethanol to give a whole volume of 10 ml and this diluted solution is then measured for the absorbance at 265 nm using a ultraviolet spectrophotometer. The absorbance is converted into E 1% value which is derived from Lambert-Beer Law and the conversion is made according to the following equation:

$$E1\% = A/cb$$

wherein A is absorbance, c is concentration in g/100 ml and b is length of optical path in cm across the test solution, which is commonly 1.

(4) Purity Measurement (4-1) Normal Phase HPLC 1 ml of the sample solution as prepared in "HPLC quantitative assay" above is dried in vacuo to remove the solvent (absolute ethanol). The residue is dissolved in 1 ml of methylene chloride. HPLC assay is carried out using 25 μl of this solution.

HPLC conditions used:
Column: YMC A-004SIL (4.6×300 mm)
Mobile phase: methylene chloride/methanol mixture (96/4)
Flow rate: 1.8 ml/min
Detection: at UV 265 nm.

(4-2) Reverse Phase HPLC

HPLC is carried out using 25 μl of the sample solution as prepared in "HPLC quantitative assay" above.

HPLC conditions used:
Column: Inertsil ODS-2 (5×250 mm)
Mobile phase: acetonitrile/water mixture (55/45)
Flow rate: 1 ml/min
Detection: at UV 265 and 220 nm.

The values of the HPLC quantitative assay and the purity measurement are averaged over two runs. The results obtained are shown in Tables 1 to 5 below.

TABLE 1

| | Results of HPLC Quantitative Assay (% Survivability) | | | | | |
|---|---|---|---|---|---|---|
| | 10° C. | | 25° C. | | 40° C. | |
| | Amor. | Crys. | Amor. | Crys. | Amor. | Crys. |
| 0 | 100 | 100 | 100 | 100 | 100 | 100 |
| 1 W | | 99.5 | 99.4 | 99.4 | 99.5 |

TABLE 1-continued

| | Results of HPLC Quantitative Assay (% Survivability) | | | | | |
|---|---|---|---|---|---|---|
| | 10° C. | | 25° C. | | 40° C. | |
| | Amor. | Crys. | Amor. | Crys. | Amor. | Crys. |
| 2 W | 98.5 | 96.8 | 94.7 | 98.8 | 88.8 | 102.9 |
| 1 M | 94.8 | 97.0 | | | | |
| 1 M (air) | 97.4 | 95.0 | | | | |

Note:
All samples were purged with argon except 1 M (air).

TABLE 2

| | E 1% | | | | | |
|---|---|---|---|---|---|---|
| | 10° C. | | 25° C. | | 40° C. | |
| | Amor. | Crys. | Amor. | Crys. | Amor. | Crys. |
| 0 | 327.5 | 359.2 | 327.5 | 359.2 | 327.5 | 359.2 |
| 1 W | | | 323.0 | 349.5 | 313.2 | 349.8 |
| 2 W | 324.9 | 343.8 | 316.9 | 341.6 | 304.0 | 348.7 |
| 1 M | 320.5 | 342.7 | | | | |
| 1 M (air) | 316.3 | 341.7 | | | | |

Note:
All samples were purged with argon except 1 M (air).

TABLE 3

| | Purity Measurement Using Normal Phase HPLC (% P.A.R at 265 nm) | | | | | |
|---|---|---|---|---|---|---|
| | 10° C. | | 25° C. | | 40° C. | |
| | Amor. | Crys. | Amor. | Crys. | Amor. | Crys. |
| 0 | | | | | | |
| ED-71 | 96.06 | 99.15 | 96.06 | 99.15 | 96.06 | 99.15 |
| Pre Form | 1.67 | 0.21 | 1.67 | 0.21 | 1.67 | 0.21 |
| Other peaks | 2.27 | 0.63 | 2.27 | 0.63 | 2.27 | 0.63 |
| 1 W | | | | | | |
| ED-71 | | | 95.97 | 99.56 | 94.47 | 99.55 |
| Pre Form | | | 1.88 | 0.14 | 2.53 | 0.14 |
| Other peaks | | | 2.14 | 0.30 | 3.00 | 0.31 |
| 2 W | | | | | | |
| ED-71 | 95.46 | 99.06 | 94.74 | 98.95 | 92.12 | 98.92 |
| Pre Form | 2.27 | 0.66 | 2.25 | 0.67 | 2.99 | 0.67 |
| Other peaks | 2.28 | 0.27 | 3.01 | 0.38 | 4.89 | 0.41 |
| 1 M | | | | | | |
| ED-71 | 94.58 | 98.91 | | | | |
| Pre Form | 2.33 | 0.65 | | | | |
| Other peaks | 3.09 | 0.44 | | | | |
| 1 M (air) | | | | | | |
| ED-71 | 95.26 | 98.88 | | | | |
| Pre Form | 2.31 | 0.66 | | | | |
| Other peaks | 2.42 | 0.46 | | | | |

Note:
All samples were purged with argon except 1 M (air).

TABLE 4

Purity Measurement Using Reverse Phase HPLC
(% P.A.R at 265 nm)

| | 10° C. | | 25° C. | | 40° C. | |
|---|---|---|---|---|---|---|
| | Amor. | Crys. | Amor. | Crys. | Amor. | Crys. |
| 0 | | | | | | |
| ED-71 | 95.38 | 99.04 | 95.38 | 99.04 | 95.38 | 99.04 |
| Pre Form | 1.16 | 0.36 | 1.16 | 0.36 | 1.16 | 0.36 |
| Other peaks | 3.47 | 0.60 | 3.47 | 0.60 | 3.47 | 0.60 |
| 1 W | | | | | | |
| ED-71 | | | 94.78 | 99.35 | 92.47 | 99.40 |
| Pre Form | | | 1.27 | 0.28 | 1.98 | 0.29 |
| Other peaks | | | 3.95 | 0.38 | 5.55 | 0.31 |
| 2 W | | | | | | |
| ED-71 | 94.48 | 98.84 | 94.20 | 98.78 | 90.68 | 98.75 |
| Pre Form | 1.75 | 0.83 | 1.72 | 0.85 | 2.53 | 0.85 |
| Other peaks | 3.77 | 0.32 | 4.08 | 0.37 | 6.78 | 0.40 |
| 1 M | | | | | | |
| ED-71 | 93.05 | 98.77 | | | | |
| Pre Form | 1.88 | 0.86 | | | | |
| Other peaks | 5.07 | 0.37 | | | | |
| 1 M (air) | | | | | | |
| ED-71 | 94.11 | 98.72 | | | | |
| Pre Form | 1.82 | 0.86 | | | | |
| Other peaks | 4.07 | 0.42 | | | | |

Note:
All samples were purged with argon except 1 M (air).

TABLE 5

| | 220 nm (%) | | | | | |
|---|---|---|---|---|---|---|
| | 10° C. | | 25° C. | | 40° C. | |
| | Amor. | Crys. | Amor. | Crys. | Amor. | Crys. |
| 0 | | | | | | |
| ED-71 | 93.95 | 97.44 | 93.95 | 97.44 | 93.95 | 97.44 |
| Pre Form | 1.37 | 0.52 | 1.37 | 0.52 | 1.37 | 0.52 |
| Other peaks | 4.70 | 2.04 | 4.70 | 2.04 | 4.70 | 2.04 |
| 1 W | | | | | | |
| ED-71 | | | 93.37 | 98.17 | 90.00 | 98.18 |
| Pre Form | | | 1.50 | 0.44 | 2.29 | 0.47 |
| Other peaks | | | 5.13 | 1.40 | 7.71 | 1.35 |
| 2 W | | | | | | |
| ED-71 | 92.85 | 97.91 | 92.39 | 97.56 | 87.40 | 97.65 |
| Pre Form | 2.02 | 1.01 | 1.93 | 1.01 | 2.88 | 1.02 |
| Other peaks | 5.13 | 1.09 | 5.68 | 1.43 | 9.72 | 1.33 |
| 1 M | | | | | | |
| ED-71 | 92.85 | 97.44 | | | | |
| Pre Form | 2.02 | 1.05 | | | | |
| Other peaks | 5.13 | 1.51 | | | | |
| 1 M (air) | | | | | | |
| ED-71 | 92.07 | 97.09 | | | | |
| Pre Form | 2.04 | 1.09 | | | | |
| Other peaks | 5.88 | 1.82 | | | | |

Note:
All samples were purged with argon except 1 M (air).

As can be seen from the tables, the crystalline form has higher stability than the amorphous from up to 2 weeks at 25° C. and 40° C.

INDUSTRIAL APPLICABILITY

The crystals of a vitamin D derivative of the present invention achieve an improved purity and stability and steady quality of the vitamin D derivative, and thus it is useful for preparing a medicament and the like containing the vitamin D derivative. Further, the method for purifying a vitamin D derivative of the present invention makes it possible to supply a highly pure vitamin D derivative in bulk (in gram order) and steadily.

Furthermore, the tachy and lumi forms which are analogues of ED-71 and the pro form of ED-71, respectively, are novel compounds and are useful for a test or analysis which may be carried out in the synthesis of a vitamin D derivative.

What is claimed is:

1. A method for purifying the compound represented by formula (II):

comprising recrystallizing a crude or preliminarily purified product of the compound represented by formula (II) from an alcohol.

2. The method according to claim 1 wherein the alcohol is methanol.

* * * * *